US012176644B2

(12) United States Patent
Yeargers et al.

(10) Patent No.: US 12,176,644 B2
(45) Date of Patent: *Dec. 24, 2024

(54) ELECTRODE CONNECTOR STRUCTURE AND CABLE ASSEMBLY

(71) Applicant: Carlisle Interconnect Technologies, Inc., St. Augustine, FL (US)

(72) Inventors: Christopher Yeargers, Portland, OR (US); Yongjie Zhou, Shenzhen (CN)

(73) Assignee: Carlisle Interconnect Technologies, Inc., St. Augustine, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 18/365,652

(22) Filed: Aug. 4, 2023

(65) Prior Publication Data

US 2023/0378678 A1    Nov. 23, 2023

Related U.S. Application Data

(63) Continuation of application No. 17/489,132, filed on Sep. 29, 2021, now Pat. No. 11,855,378.

(51) Int. Cl.
*H01R 13/24* (2006.01)
*H01R 13/627* (2006.01)
*H01R 43/24* (2006.01)

(52) U.S. Cl.
CPC ..... *H01R 13/2442* (2013.01); *H01R 13/6273* (2013.01); *H01R 43/24* (2013.01); *H01R 2201/12* (2013.01)

(58) Field of Classification Search
CPC .. H01R 4/4809; H01R 4/4881; H01R 4/4845; H01R 4/4818; H01R 11/22; H01R 11/24;

(Continued)

(56) References Cited

U.S. PATENT DOCUMENTS 4,220,387 A    9/1980    Biche et al.
4,385,793 A    5/1983    Koford et al.
(Continued)

FOREIGN PATENT DOCUMENTS

EP    1929942 A1    6/2008
WO    2019148924 A1    8/2019

OTHER PUBLICATIONS

European Patent Office; Search Report and Written Opinion in related International Patent Application No. PCT/US2022/045135 dated Jan. 18, 2023; 11 pages.

*Primary Examiner* — Gary F Paumen
(74) *Attorney, Agent, or Firm* — Wood Herron & Evans LLP

(57) ABSTRACT

A connector assembly for coupling with one or more electrodes includes one or more cables with wires. A plug is electrically coupled with an end or ends of the cables. An electrode connector structure is electrically coupled with the cables and includes a body that is configured for forming an internal space. A cantilevered first arm has an end that cantilevers toward the internal space. The cantilevered first arm has a rest position and a flexed position. A stationary second arm and arm end extend into the internal space opposite the first arm. At least one of the ends of the cantilevered first arm and stationary second arm include an electrical contact. In the rest position, the end of the cantilevered first arm is positioned opposite the stationary second arm a first distance. In the flexed position, the cantilevered arm, moves away from the stationary second arm to separate the ends to a greater distance to receive the electrode and returns to the rest position to grip the electrode.

20 Claims, 16 Drawing Sheets

(58) Field of Classification Search
CPC ............. H01R 25/003; H01R 13/2442; H01R 13/6273; H01R 43/24; H01R 2201/12
USPC ....... 439/816, 830, 834, 859–861, 592, 593, 439/505
See application file for complete search history.

(56) References Cited

U.S. PATENT DOCUMENTS

| | | | |
|---|---|---|---|
| 4,637,672 | A | 1/1987 | Peterman et al. |
| 4,674,817 | A | 6/1987 | Olms |
| 6,083,015 | A | 7/2000 | Vargas et al. |
| 7,285,021 | B2 | 10/2007 | Bell et al. |
| 8,376,782 | B2 | 2/2013 | Govekar |
| 11,855,378 | B2 * | 12/2023 | Yeargers ............ H01R 13/6273 |
| 2012/0178287 | A1 | 7/2012 | Mantay et al. |
| 2015/0255916 | A1 | 9/2015 | Kao et al. |
| 2021/0095740 | A1 | 4/2021 | Graßl |

* cited by examiner

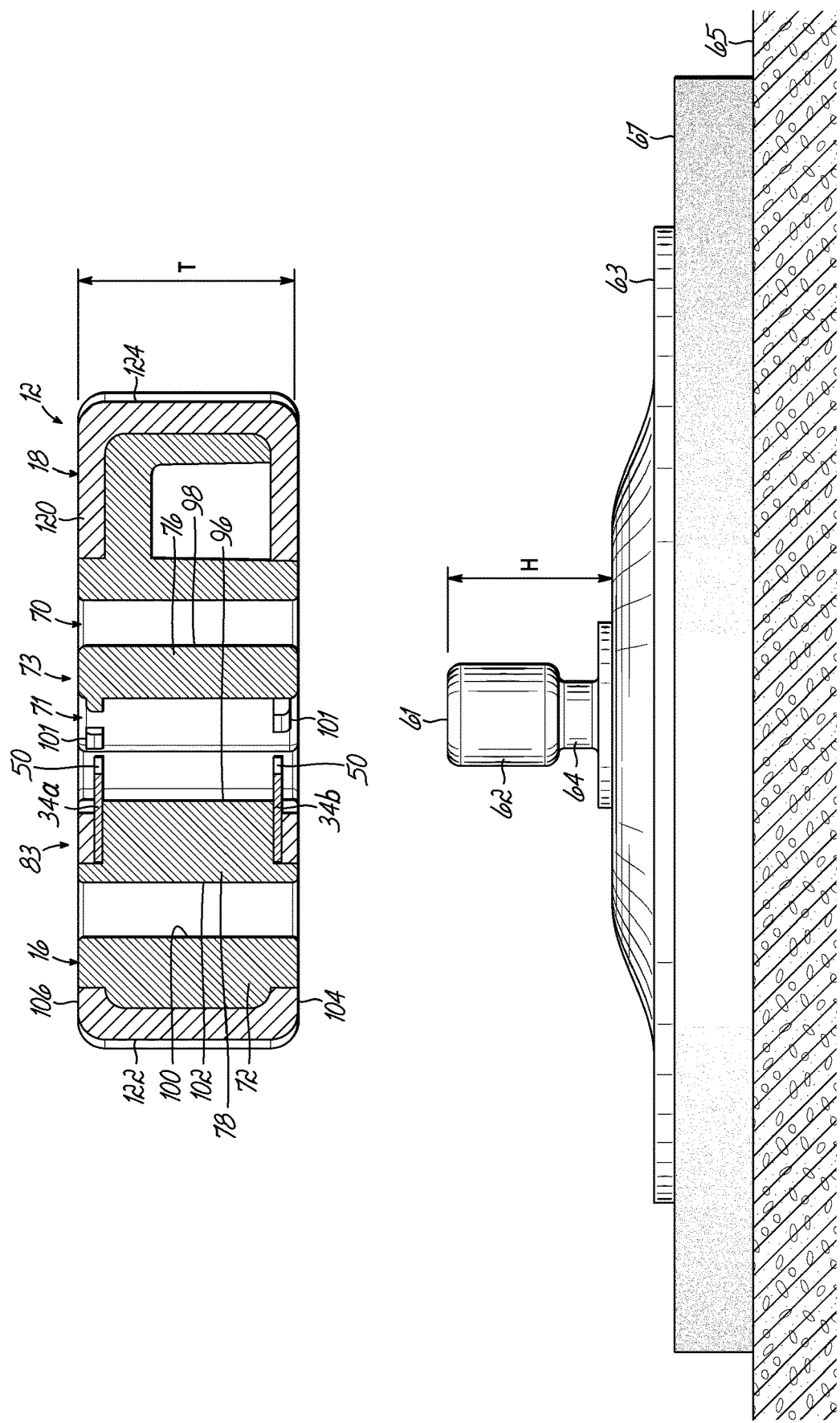

ELECTRODE CONNECTOR STRUCTURE AND CABLE ASSEMBLY

CROSS-REFERENCE TO RELATED APPLICATIONS

This application is a Continuation of U.S. patent application Ser. No. 17/489,132 filed Sep. 29, 2021 (pending), the disclosure of which is incorporated by reference herein.

TECHNICAL FIELD OF THE INVENTION

The present invention is directed to a connector for coupling cables and a cable assembly to electrodes, such as electrodes used to capture electrical signals from an animal body.

BACKGROUND OF THE INVENTION

Various connector devices are used for electrical connections of connecting lines to electrodes, in particular medical engineering skin electrodes. Such connecting devices are used, for example, for measurement of physiological signals from living animals or human beings, such as heart action voltages (electrocardiogram, EKG). The electrodes are positioned on the patient's skin, by an adhesive, for example, and are connected to an electric connecting line over which the physiological electrical signals are conducted to a medical device for further processing and evaluation. The connector devices generally operate as snap-on connectors that are snapped onto the contact post or pin of the electrode and retain the cable connected to the electrode. The contact post may be a separate element of the electrode or may form the electrode surface itself in conjunction with a base component.

The use of such electrode connectors places heavy demands on such devices. Thus, the installation and removal of the connection should be relatively easy without application of a significant force. Furthermore, the electrode connector should produce a durable high quality electrical connection between the electrode and cable.

Consequently, there is always a need for improved electrode connectors and retainers to provide a simple yet robust electrical connection that may be readily installed on and removed from an electrode post. The present invention addresses such needs and provides a simple to use electrode connector that grips or grabs an electrode with a direct gripping action that is readily applied and removed by a single handed pinch of opposing sides of the connector.

SUMMARY OF THE INVENTION

A connector for coupling with an electrode includes a body that is configured for forming an internal space. A cantilevered first arm of the body has an end and is coupled to the body for cantilevering toward the internal space. The cantilevered first arm has a rest position and a flexed position. A stationary second arm has an end and extends on the body into the internal space. The stationary second arm includes and electrical contact. In the rest position, the end of the cantilevered first arm is positioned opposite the end of the stationary second arm a first distance in the internal space. The connector can be gripped and pinched or squeezed to move the cantilevered first arm to the flexed position. In the flexed position, the cantilevered arm moves the end thereof away from the end of the stationary second arm to separate the ends to a second distance greater than the first distance for receiving an electrode structure. When the pinch force on the connector arms is decreased, the cantilevered first arm is configured for returning to the rest position to grip the electrode and hold the electrical contact against the electrode.

BRIEF DESCRIPTION OF THE DRAWINGS

FIG. 3C is a side view in partial cross-section of the connector structure of FIG. 3A of the invention in relation to an electrode.

DETAILED DESCRIPTION OF THE INVENTION

Figure 1:
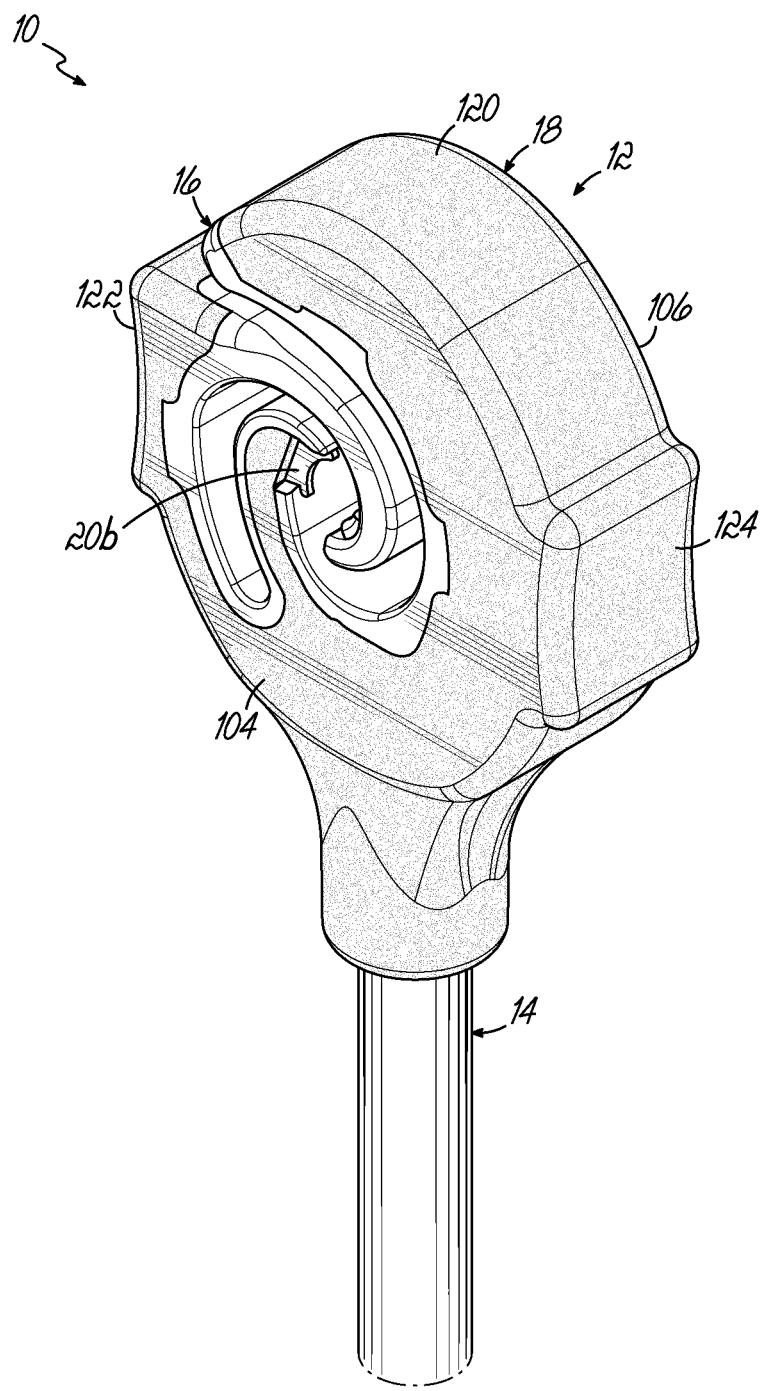
FIG. 1 is a perspective view of a connector structure for electrically interfacing with an electrode in accordance with an embodiment of the invention.
Figure 2:
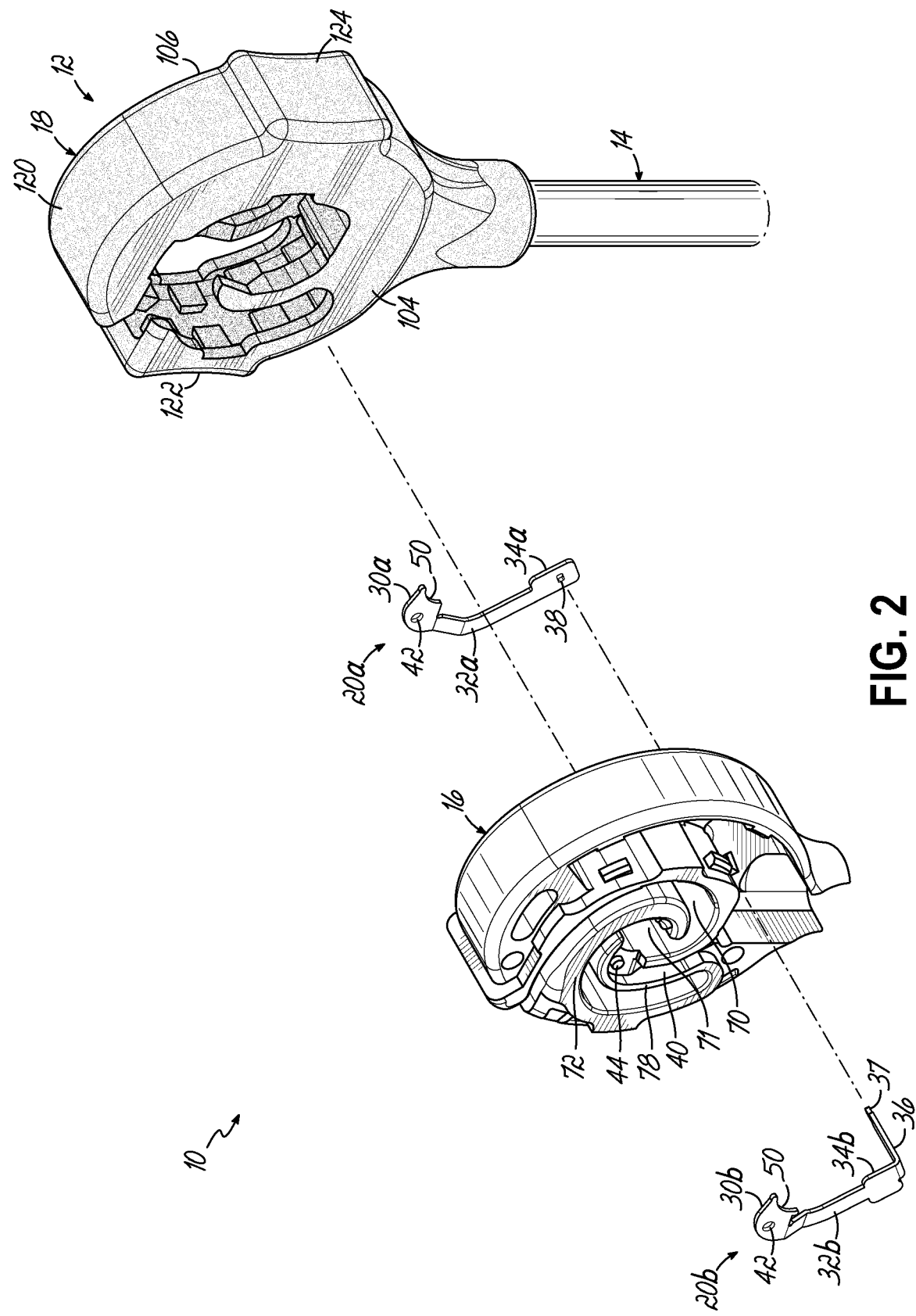
FIG. 2 is an exploded perspective view of the connector structure of FIG. 1 showing the internal body, housing and electrical contacts.

FIG. 1 illustrates an electrode retainer or connector 10 in accordance with one embodiment of the invention. The electrode connector is configured to grab onto an electrode, such as an Electrocardiogram (ECG) electrode or other electrode for obtaining and conducting electrical signals from an animal body for further processing (see FIG. 5C). To that end, the electrode connector 10 incorporates a connector structure 12 that is coupled with a cable 14. While a single electrode connector 10 is illustrated in FIGS. 1 and 2, for example, generally such a connector will be utilized in an assembly that includes a plurality of electrode connectors to engage with a plurality of electrodes that are positioned on the human body of a patient, for example. (See FIGS. 7A, 7B) As described further herein, different assembly layouts may be utilized to provide the desired number of electrode retainers for the particular signal capture and processing and related medical procedure.

Turning to FIG. 2, the connector structure 12 generally incorporates a body structure or body 16 that provides the electrical connecting and gripping functionality of the electrode connector structure 12. The body forms elements that operate to grab or grip an electrode and the body is captured or encapsulated within an outer housing 18. Each of the body 16 and housing 18 interface with a cable 14 that will generally contain one or more wires or conductors for electrical signal capture and conduction. Each of the electrode connectors 12 includes one or more metal electrical contacts in an electrical contact assembly 20 that are connected to a wire and that grab onto or grip the conductive post of an electrode when in use. (See FIGS. 3C, 4C, and 5C).

Figure 2B:
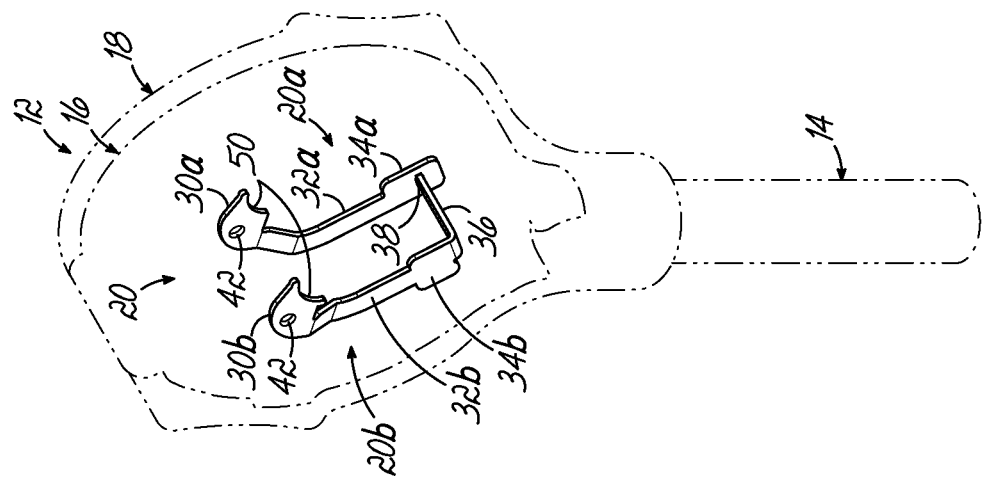
FIG. 2B is a perspective view, partially in phantom, showing the arrangement of electrical contacts on either side of the connector structure.

Specifically, referring to FIG. 2, the contacts 20*a*, 20*b* are positioned proximate each of the opposing faces or sides of the electrode connector structure 12. In that way, the electrode connector structure 12 may be used to engage an electrode post from either face or side of the connector to provide the desired electrical connection and signal capture from the electrode. Referring to FIG. 2, for interfacing with an electrode, the individual contacts 20*a*, 20*b* each include a grip head 30*a*, 30*b* and a respective elongated body 32*a*, 32*b*. Each of the bodies terminates into pads 34*a*, 34*b*. At least one of the contacts 20 incorporates an extension leg 36 to span the thickness of the body 16 and electrically couple with the opposing contact so that both contacts are electrically the same. To that end, contact 20*a* may include an aperture 38 to receive an appropriately formed tip 37 of the leg 36 of contact 20*b* as shown in FIG. 2B. In that way, the two contacts 20*a*, electrically couple together other ways of forming the contacts may be used. For example, the two contacts and extension leg might be a unitary structure.

Figure 2A:
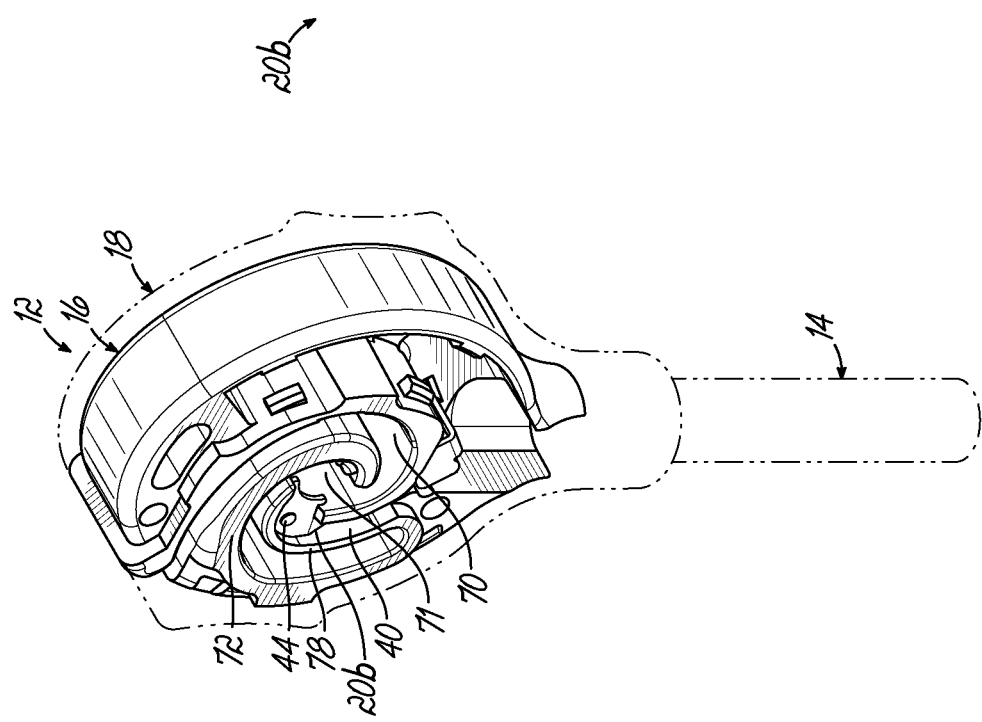
FIG. 2A is a perspective view, partially in phantom, showing the internal body and positioning of the electrical contacts.

Referring to FIGS. 2A and 2B, the body 16 is appropriately formed with spaces and openings to contain the contacts. More specifically, the contacts 20*b* each are captured in appropriately formed slots 40 that are formed within body 16. FIG. 2A shows one slot, but there is a similar slot on the opposing side or face of body 16 to receive contact 20*b*, so the contacts are secured in body 16 in the orientation shown in FIG. 2B. Referring to FIG. 2, each of the contacts incorporates an alignment aperture 42 that engages an alignment button 44 or other structure also formed within body 16 proximate to where the heads 30*a*, 30*b* of the contacts are positioned on either side of the body 16. In that way, the contacts 20*a*, are properly positioned within body 16 and are configured for engagement with the metal of an electrode post as discussed herein.

To that end, referring again to FIG. 2B, each of the electrical contact heads 30*a*, 30*b* incorporates an arcuate edge 50 that is configured to extend around an arcuate outer surface of an electrode 60 as shown in FIG. 3C, for example. More specifically, each of the electrodes 60 includes an up standing post 61 having a head portion 62 with a particular outer diameter, and then a smaller diameter waist portion 64 on which the contact 30*a*, 30*b*, and particularly the arcuate edge 50 will rest when the electrode is engaged by a connector structure 12 and the connector structure is released from being gripped and squeezed. Generally, the electrode post 61 has a height "H" which is smaller than the thickness "T" of the connector structure 12 is shown in FIG. 3C. In that way, as illustrated in FIG. 5C, the post 61 is completely contained by the thickness of the connector structure 12 with one of the contacts 20 gripping the waist portion 64 of the post 61.

Figure 5A:
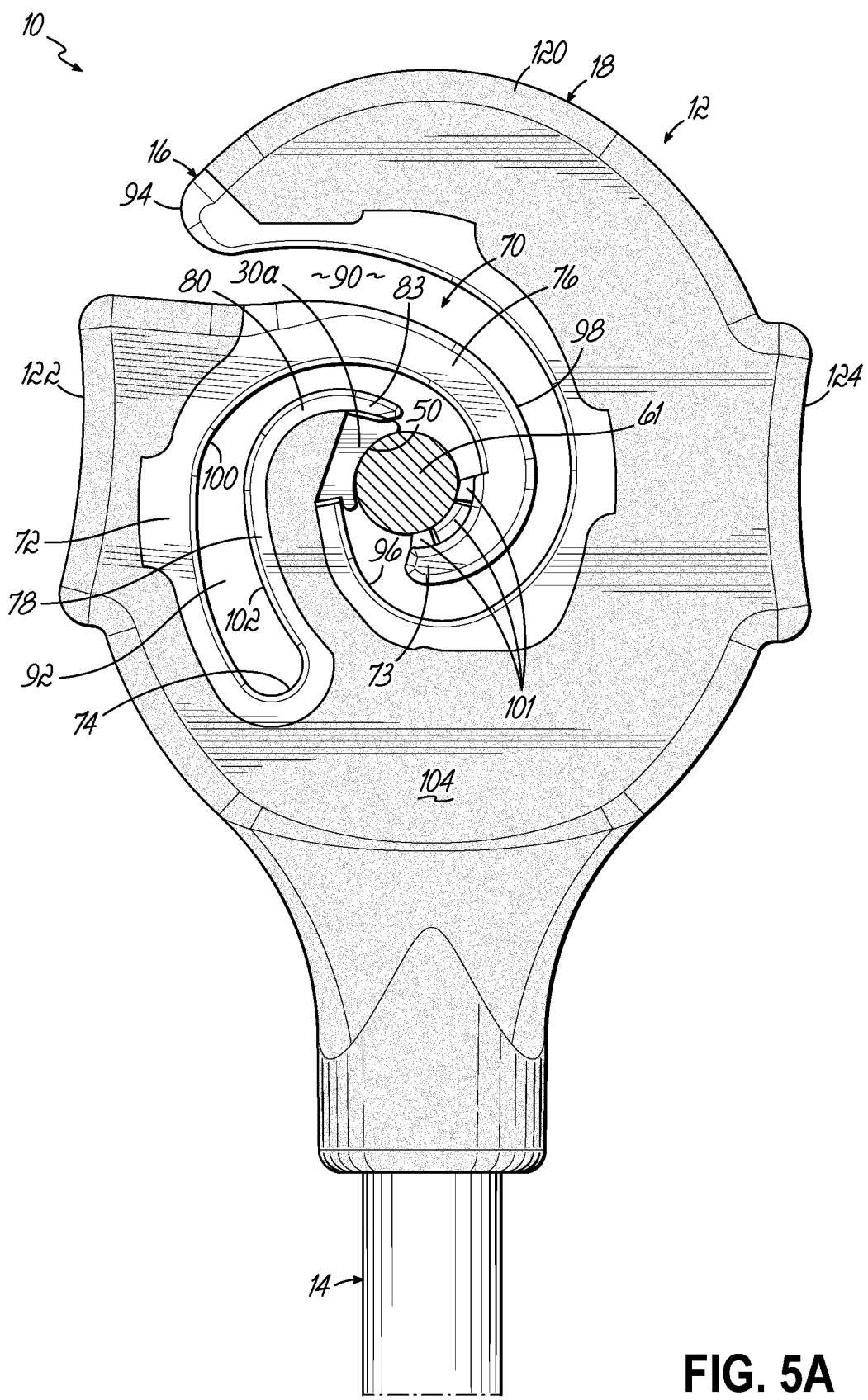
FIG. 5A is plan view of the electrical connector of FIG. 3A showing the removal of the gripping forces for a return of the cantilevered arm to a rest position gripping the electrode.
Figure 5B:
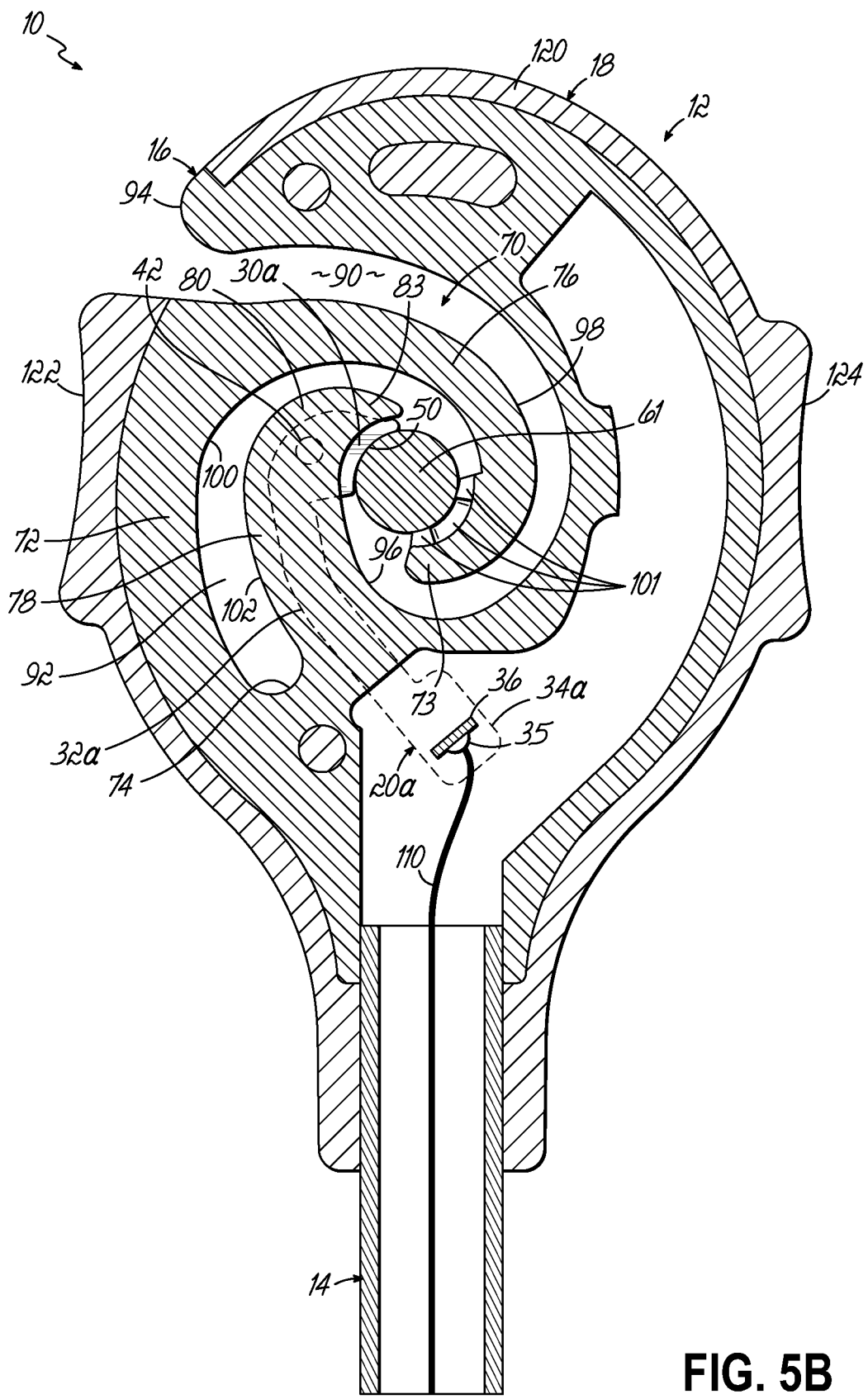
FIG. 5B is a cross-sectional plan view of the electrical connector of FIG. 5A.
Figure 5C:
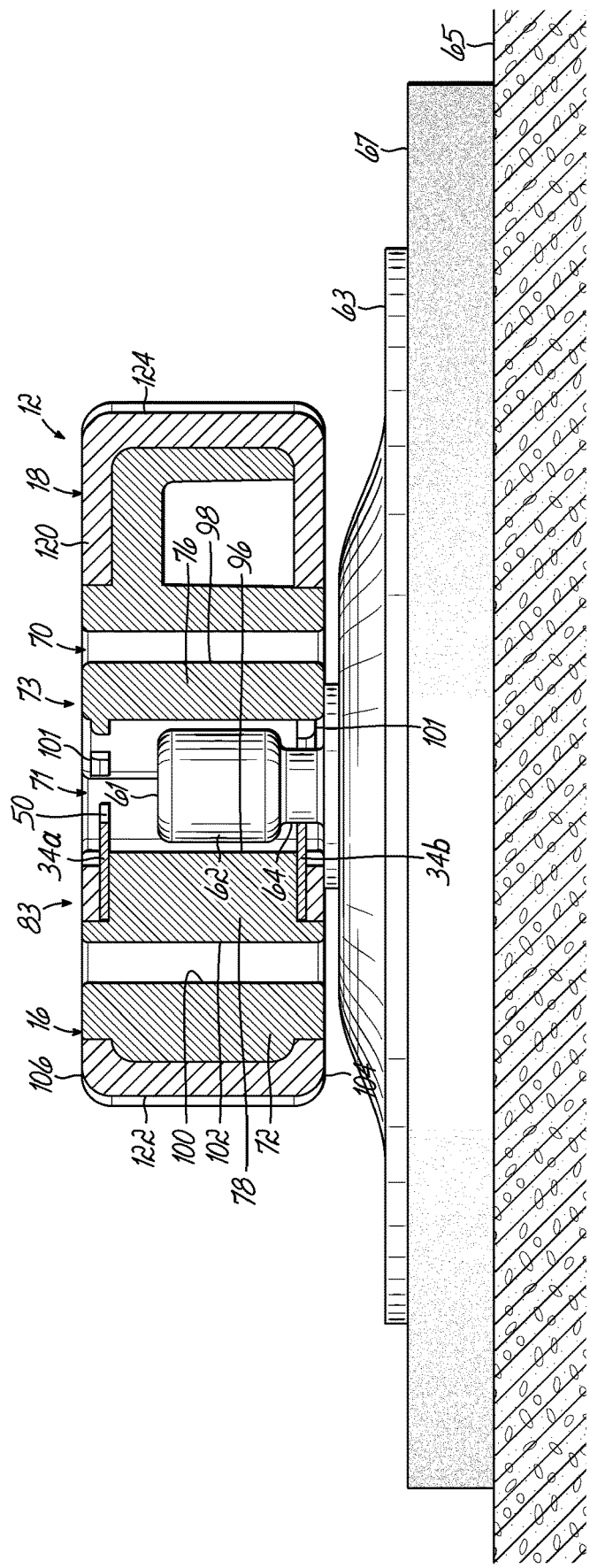
FIG. 5C is a side view in partial cross-section of the connector structure of FIG. 5A of the invention in relation to an electrode.

Referring to FIGS. 2A-2B, the electrode connector structure 12 includes a preformed body 16 that is formed and configured to create an internal space and a plurality of arms that operate together in the internal space to grip an electrode post 61 as illustrated in FIG. 5C. Specifically, and with reference to FIG. 3A, the body 16 is formed of generally rigid material to create an internal space 70 in which the arms are positioned to operate. The arms include a first arm 72 that has a base proximate to a hinge point 74 that connects the first arm to the body 16 so that the first arm is cantilevered with respect to the body 16. Specifically, the cantilevered first arm 72 hinges proximate to the formed hinge point 74 and the arm 72 cantilevers toward the internal space 70. The arm 72 extends on body 16 in a generally arcuate or spiral path extending inwardly toward internal space 70 around a stationary second arm 78. In that way, the arms 72, 78 are integrally formed with the body 16.

Figure 3A:
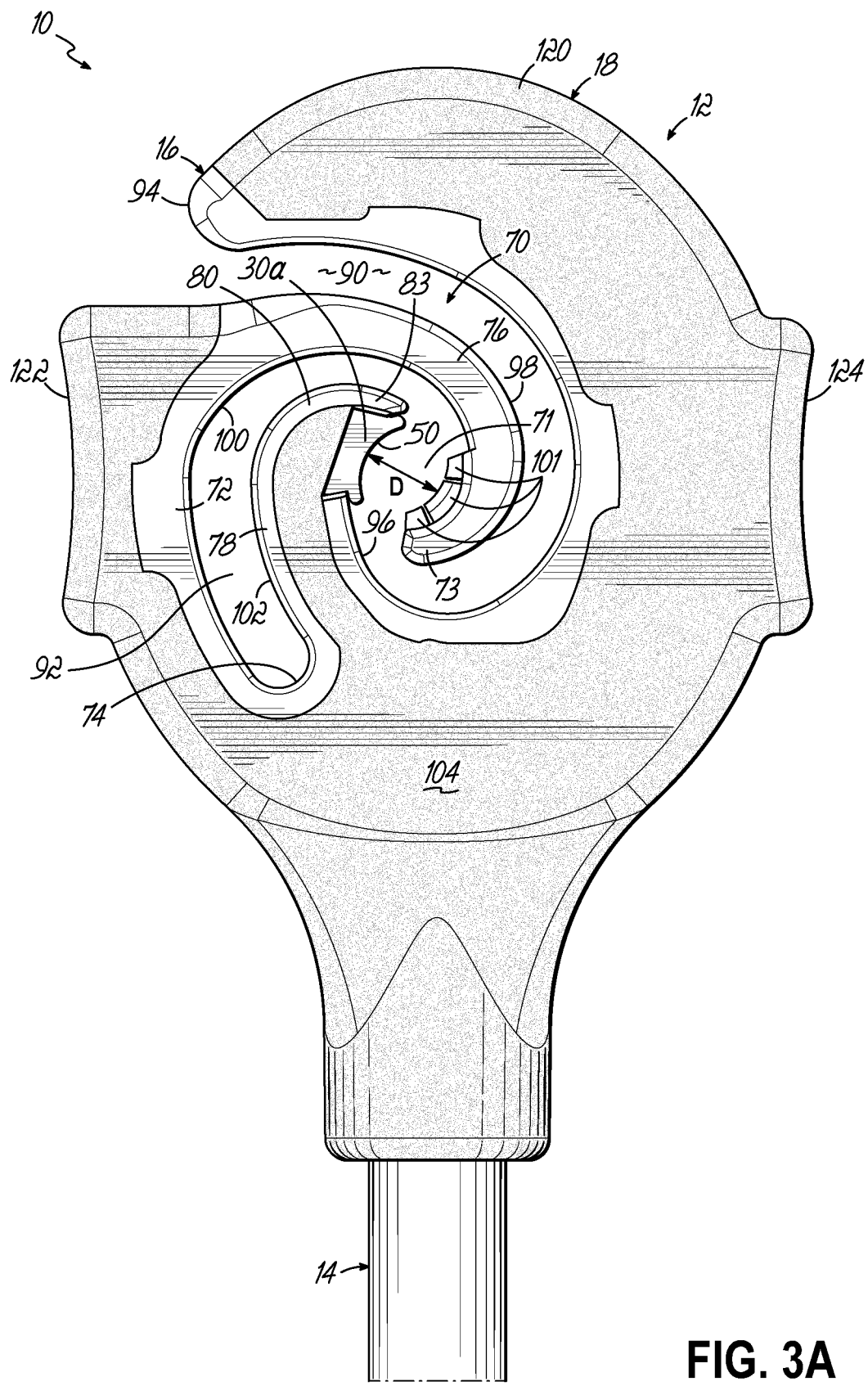
FIG. 3A is a plan view of a connector structure of FIG. 1 in accordance with an embodiment of the invention.

More specifically, as shown in FIGS. 2 and 3A, the cantilevered first arm 72 includes an arcuate portion 76 that originates on an outer edge of connector structure 12 and extends in a somewhat spiral path into the internal space 70. Body 16 also includes and forms a stationary second arm 78 that also extends into the internal space 70 next to the first arm 72. The stationary second arm 78 includes a base connector to the body 16 and an arcuate portion 80 that extends to present an end 83 of the stationary second arm opposite to the end 73 of the cantilevered first arm. Particularly, the cantilevered first arm 72 includes an inner end 73 positioned opposite an inner end 83 of the stationary second arm 78. Referring to FIG. 3A, the body is formed so that the base of the first arm 72 originates on an outer edge of the body and the arm arcs in the spiral path inwardly toward a center of the body. The first arm 72 extends alongside the second arm 78 for a section of its length and curves or spirals into space 70 and over and around the second arm 78 and over and around the end 83 of the second arm. The curve or spiral of the cantilevered first arm positions the terminal end 73 of the cantilevered first arm generally opposite to the terminal end 83 of the stationary second arm. Each of the terminal ends 73 and 83 are positioned within the internal space 70 such that they create an electrode receiving space 71 generally in the center of the connector structure 12. As discussed herein, the first arm 72 and second arm 78 operate together to grip the electrode post 61 and provide an electrical connection at the electrode 60. The cantilevered first arm 72 has a rest position and a flexed position. FIG. 3A shows the first arm 72 in the rest position where it is near end 83 and separated by a distance D in space 70

Referring to FIG. 2, the body 16 may be pre-formed of a suitable material, such as a glass-filled polyurethane material, for example, BASF R3000. As illustrated in FIG. 3A, the internal space 70 is formed within body 16 in the form of arcuate or spiral space sections 90, 92 that extend generally spirally within the body 16 to form somewhat nesting spirals that create both the cantilevered first arm 72 and the stationary second arm 78. Specifically, the body 16 has a generally circular cross-section and the arcuate space sections 90, 92 spiral internally in that circular section to form the arms. Specifically, arcuate space section 90 extends from the outer edge 94 of the body 16 and progresses in a spiral internally into the space 70 to form an inside edge 96 of the stationary second arm 78. At the same time, arcuate space section 90 also forms an outside edge of the cantilevered first arm 72 and particularly, the arcuate portion 76 of that cantilevered first arm.

Arcuate space section 92, on the other hand, begins proximate hinge point 74 and progresses in a spiral path toward the center of the internal space 70 to form an inside edge 100 of the cantilevered first arm 72 and an outside edge 102 of the stationary second arm 78. The termination of the arcuate space section 92 within the body 16 forms an arc or curve where edges 100, 102 meet and forms the hinge point 74 from which the cantilevered first arm 72 hinges from body 16 as shown. More specifically, referring to FIG. 3A, the inside edge 100 of the cantilevered first arm 72 meets with the outside edge 102 of the stationary second arm 78 to form hinge point 74 generally at the base end of the first arm 72.

Figure 4A:
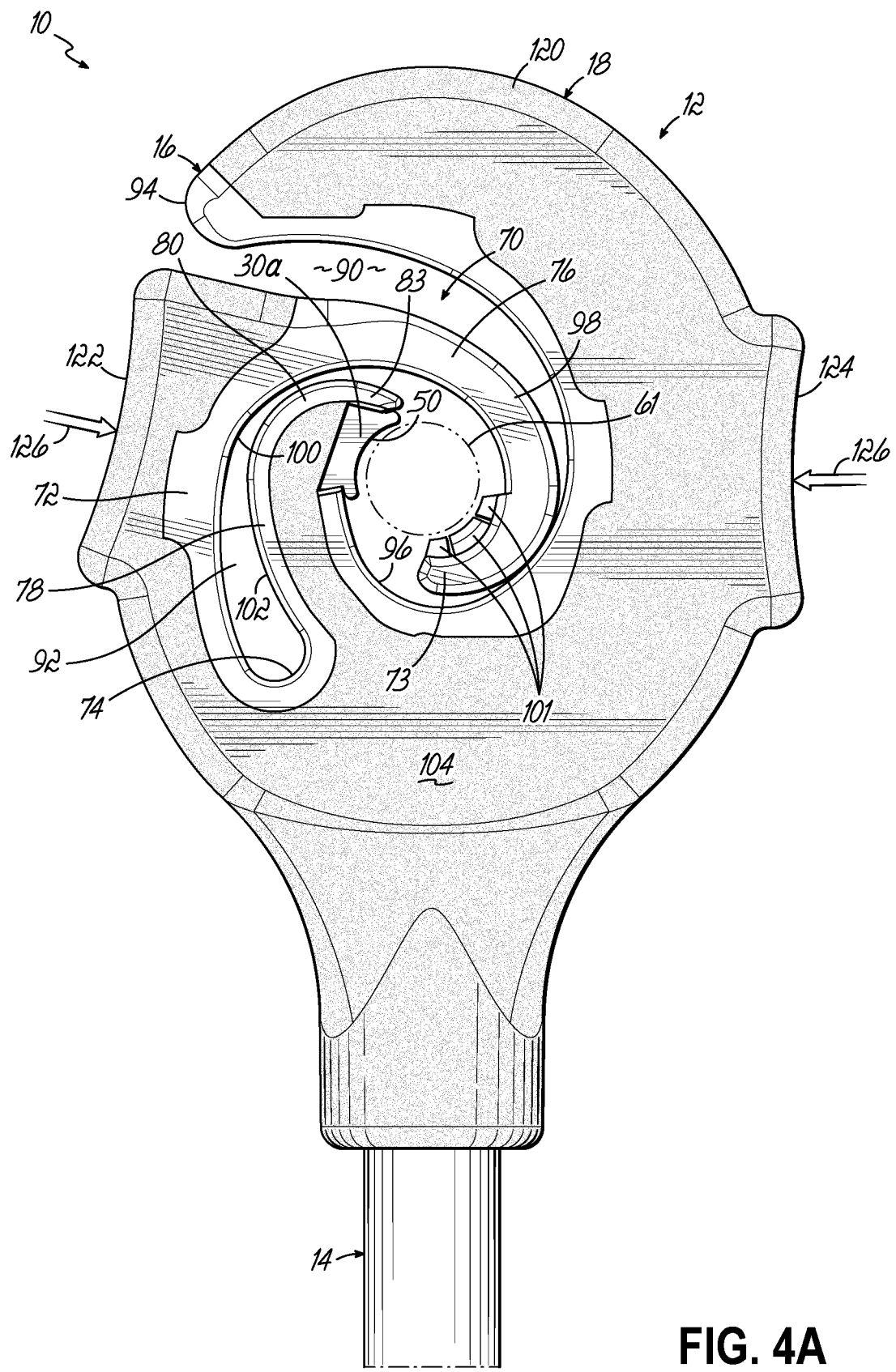
FIG. 4A is a plan view of the electrical connector of FIG. 3A showing gripping forces and movement of the cantilevered arm for engaging an electrode.
Figure 4B:
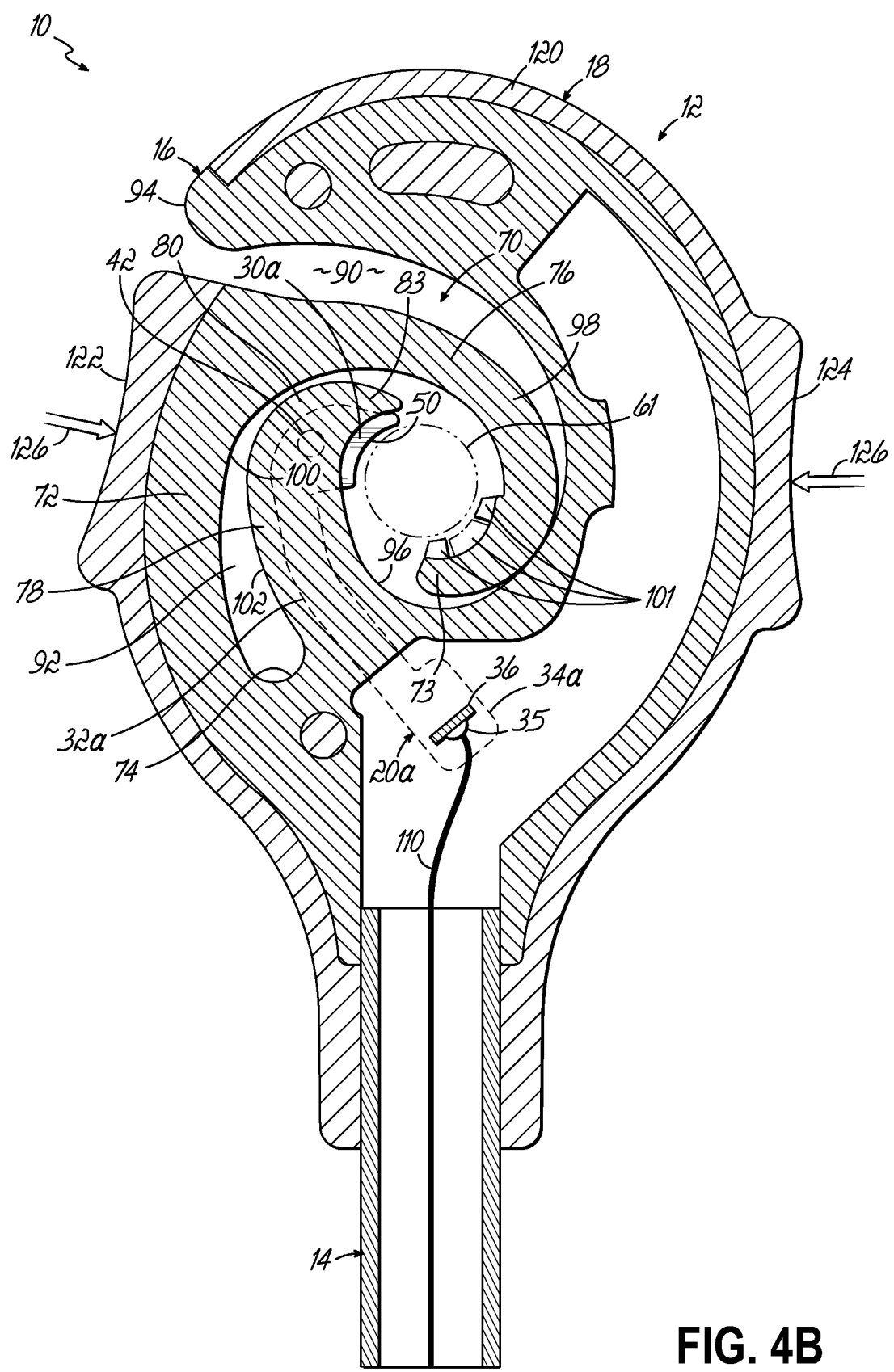
FIG. 4B is a cross-sectional plan view of the electrical connector of FIG. 4A.
Figure 4C:
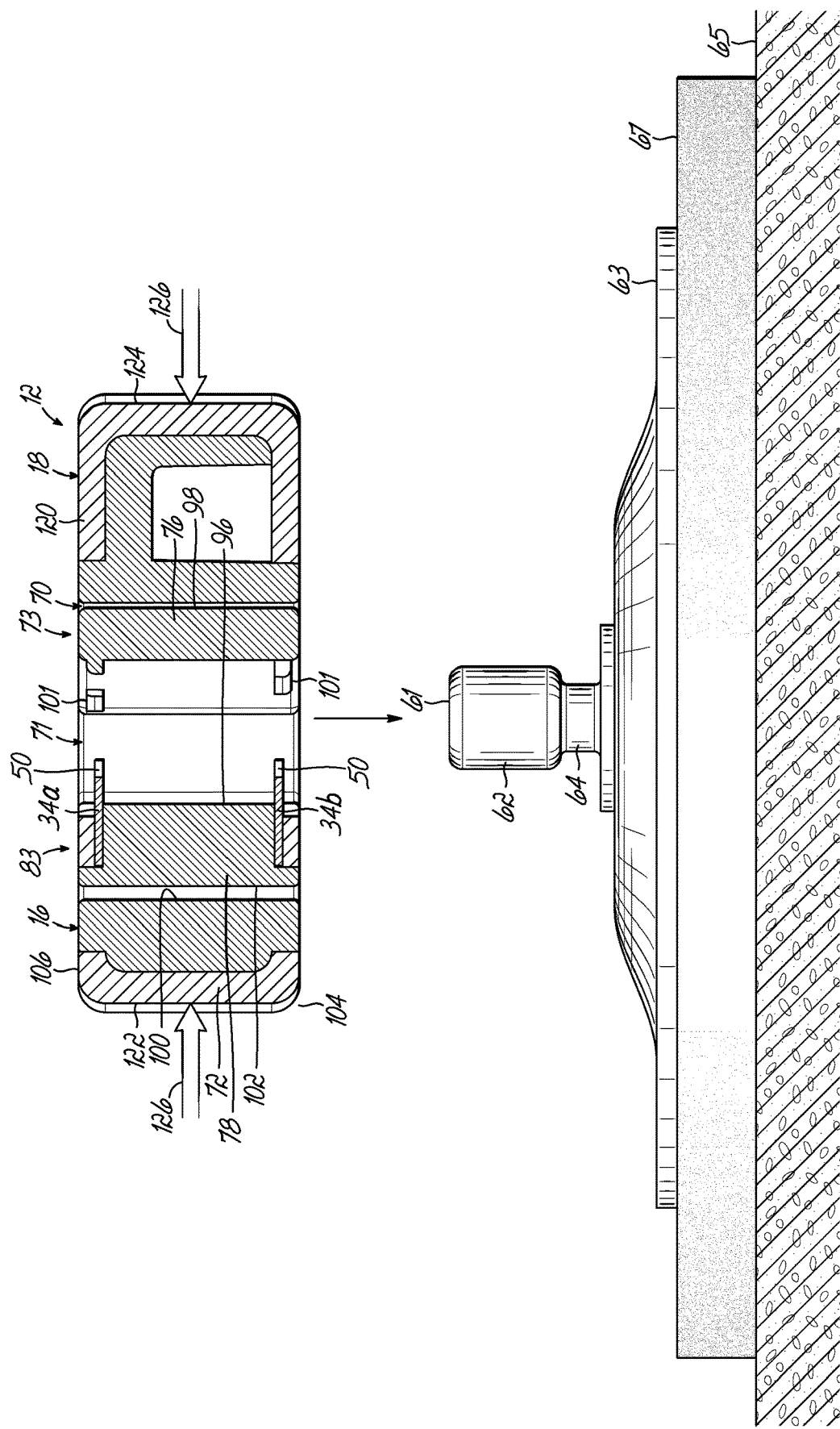
FIG. 4C is a side view in partial cross-section of the connector structure of FIG. 4A of the invention in relation to an electrode.

The inside edge 100 and outside edge 98 progress around the cantilevered first arm 72 to meet generally at the terminal end 73 of the first arm 72. Similarly, the outside edge 102 and the inside edge 96 of the stationary second arm 78 progress around the internal space 70 to form a terminal end 83 to the second arm 78. The arcuate portions 76, 80 of the respective first arm 72 and second arm 78 are curved so as to present the terminal ends 73, 83 proximate electrode receiving space 71. The ends 73, 83 are positioned to oppose each other in the rest position of arm 72 as shown in FIG. 3A. The cantilevered first arm 72 may then be moved or pushed inwardly into space 70 to a flexed position and toward the second arm 78. (See FIG. 4A). The first arm 72 flexes at the hinge point 74. The end 73 of the first arm then moves in a direct line of travel with respect to end 83 so that terminal end 73 moves directly away from terminal end 83 to expand the space 71 and receive the electrode post 61. That is, the cantilevered first arm 72 has a flexed position where it is pushed toward arm 78 to move the end 73 away from end 83 as shown in FIGS. 4A-4C to form a space 71 having a distance greater than the distance D between the ends 73, 83 in the rest position.

More specifically, referring again to FIG. 3A, the terminal ends 73 and 83 of the respective arms are shown opposite each other around the electrode receiving space 71. As shown in FIG. 3C, connector structure 12 may be positioned over electrode 60, and particularly over the electrode post 61. Electrode may be any suitable electrode structure for capturing electrical signals from a body, such as during an EKG procedure. Generally, electrode 60 will incorporate a post structure 61 that is coupled to a base 63 that may be adhered to skin surface 65 of a human or other animal through an appropriate adhesive layer 67. In that way, electrical signals from the skin surface 65 are presented to the post 61, and may be captured by the connector structure 12 that may be clipped or connected to post 61.

To that end, the connector structure 12 includes the one or more contacts 20a, 20b as mentioned herein for capturing electrical signals from post 61. Referring again to FIGS. 2A and 2B, the unitary body 16 may be appropriately formed for forming both the cantilevered first arm 72 and the stationary second on 78. At least one of those arms will include the electrical contacts 20a, 20b. In the disclosed embodiment, the stationary second arm 78 is configured to contain the contact assembly 20 whereas the cantilevered first arm 72 incorporates one or more teeth 101 for opposing the contacts 20a, 20b and gripping the post 61. The opposing contacts and teeth come together in the rest position for holding the post it securely to the stationary second arm 78 and respective contact 20a, 20b. Alternatively, the first arm might include the contacts and the second arm might include the teeth. Referring to FIG. 2B, the contacts are made of an electrically conductive material, such as nickel plated stainless steel SST 303, and are secured within body 16 with one contact being positioned generally proximate each of the face surfaces or sides 104, 106 of the connector structure 12. As noted, the preformed body 16 forms the slots 40 for receiving the contacts 20a, 20b. The contacts are positioned in the appropriate slots and the leg 36 spans across the thickness of the body to connect the contacts as shown in FIG. 2A to present a single conductive structure 20 as shown in FIG. 2B made up of each of the individual contacts 20a, 20b. The contacts are coupled to one or more wires or conductors of cable 14 such as by soldering the wires to a portion of the contact assembly 20. As discussed herein, the connector structure 12 and its features may be incorporated into terminal electrode connectors, such as those shown in FIGS. 1 and 2 wherein the cable 14 terminates at the connector structure 12. In that scenario, an internal wire of cable 14 is connected to contacts 20a, 20b.

Figure 7A:
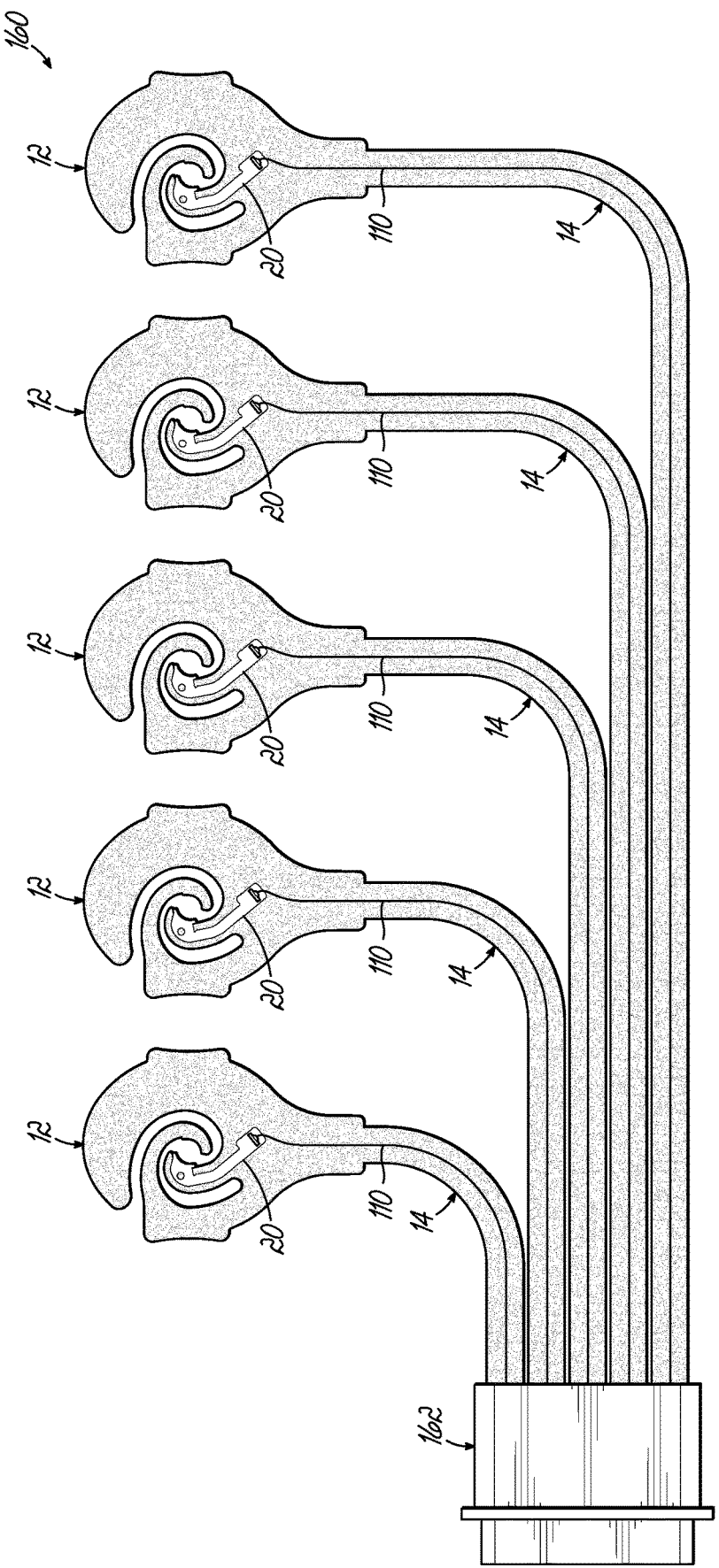
FIG. 7A is a plan view, in partial cross-section, of a connector assembly incorporating connector structures in accordance with an embodiment of the invention wherein the connector structure terminates each cable of the assembly.
Figure 7B:
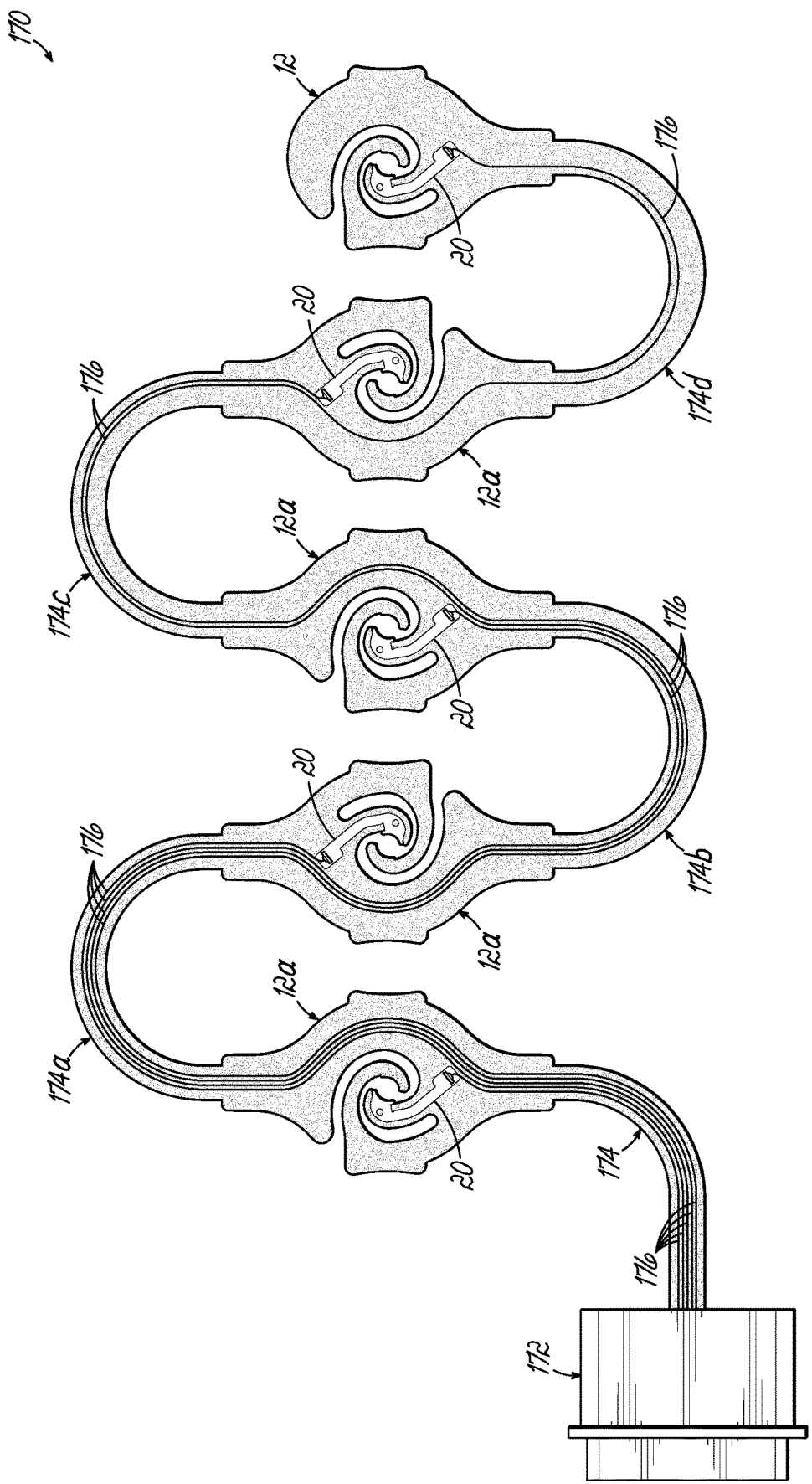
FIG. 7B is a plan view, in partial cross-section, of a connector assembly incorporating connector structures as illustrated in FIGS. 6A and 6B showing sequential positioning of connector structures along a single cable of the assembly.

Referring to FIG. 2B, a wire 110 of cable 14 is shown coupled to the contact assembly 20, such as with a pad 34a, 34b or the extension leg 36, and may be physically and electrically coupled, such as through soldering, so that cable 14 and wire 110 are electrically coupled with the contacts the connector structure 12. As discussed herein, the inventive connector structure of the invention may be implemented with a larger assembly, including a plurality of connector structures. In one embodiment as shown in FIG. 7A, for example, each of the connector structures will terminate the respective cable. Alternatively, a passthrough assembly is illustrated in FIG. 7B. Wires from a cable will terminate in a connector structure while other wires will pass through to connect to connector structures further down the cable. In any case, each of the connector structures is electrically coupled with one or more wires 110 for capturing the electrical signals from a body-mounted electrode.

In accordance with one aspect of the invention, the cantilevered first arm 72 is flexible proximate a base of the arm near hinge point 74 for flexing to a flexed position with respect to the stationary second arm 78. In that way, body 16 may be gripped and engaged with a squeeze force directed to the cantilevered first arm 72 for flexing the arm 72 and thus moving the arm end 73 further into space 70 and further away from the end 83 of the stationary second arm 78. The material of the body 16 is flexible to allow such flexing and cantilever action of the arm to the flexed position. Once the cantilevered arm is released, it is biased by the material of the body to the rest position and flexes back toward its original or rest position to grip the electrode 60 as discussed herein.

Figure 3B:
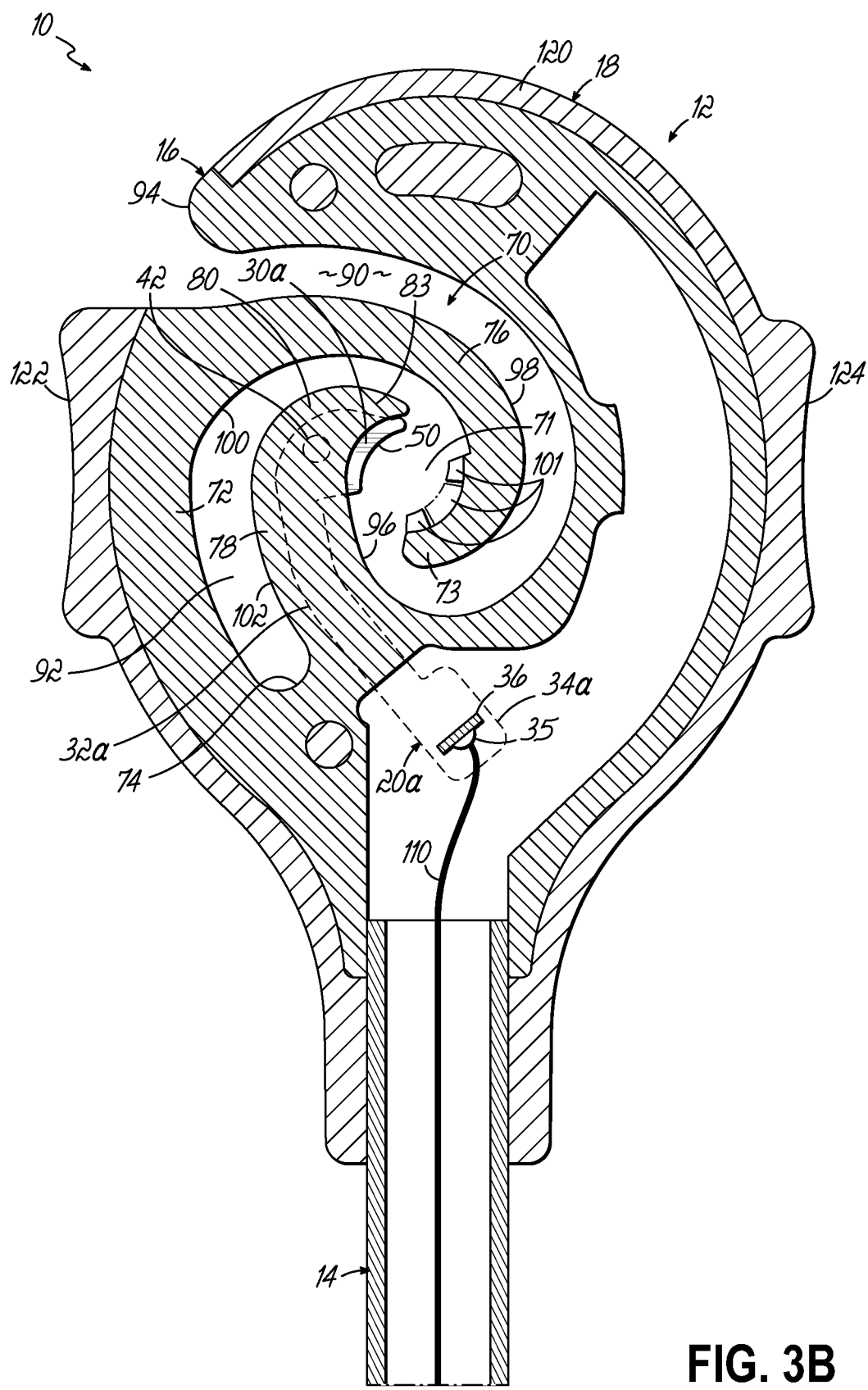
FIG. 3B is a cross-sectional plan view of the electrical connector of FIG. 3A.

In accordance with another aspect the invention, the preformed body 16 may be over molded with an over mold material to form the outer housing 18 as illustrated in FIGS. 3A and 3B. The over mold material may be a suitable electrically insulative material, such as an elastomeric urethane, for example BASF C78. Once the contacts 20a, 20b are properly positioned within their respective slots 40 in the body 16 and one or more wires of cable 14 are connected to the contacts, the over mold material may be applied to form the outer housing 18 and contain the contacts in position and to cover the body 16 and part of cable 14 to secure the connector structure 12 with the cable 14 and to hold all the various parts together. The individual wires 110 of cable 14 may be appropriately attached, such as by soldering, with the various contacts. The housing structure indicated in FIG. 3B by reference numeral 120 fills in or otherwise interfaces with various openings in the body 16 and covers portions of the body as well as covering the slots 40 and contacts 20a, 20b as shown in FIGS. 3A and 3B. As shown in FIG. 3A, certain areas of the body 16 remain exposed with respect to the over mold. For example, the contacts 20a, 20b are exposed as are teeth 101 of arm 78. The various edges of the arms are also exposed as seen in FIG. 3A. The housing 18 does not interfere with the movement of the arm 72 between rest and flexed positions. The housing also forms gripping portions 122, 124 proximate opposing sides of the connector structure 12 for providing a visual indication of where the connector structure is to be gripped and squeezed to move the cantilevered first arm 72. One of the gripping portions 122 is positioned proximate the cantilevered first arm 72 so that a gripping force applied to the gripping portions moves the cantilevered first arm to the flexed position. Specifically, a user would grab the connector structure with fingers at the gripping portions 122, 124 to squeeze the gripping portions toward each other and thus move the cantilevered first arm 72 toward from the stationary second arm 78 thus moving the terminal ends 73, 83 apart.

In accordance with one aspect of the invention, the end 73 of the cantilevered first arm 72 will move in a direct line of travel away from end 83 of the stationary second arm 78 and the contacts 20a, 20b. Referring specifically to FIG. 4A, a force applied between the two gripping portions 122, 124 will hinge the cantilevered first arm 72 at hinge point 74 to the flexed position. Again, in that way, the cantilevered first arm 72 moves generally toward the stationary second arm 78 as shown. However, because of the unique arcuate shape of the cantilevered first arm, and particularly the arcuate portion 76 that spirals over and around arm 78 and contains the end 73, the terminal end 73 and the respective teeth 101 move in the direction of arrow 130 away from contact 20a. FIG. 4B shows in cross-section, the movement to the flexed position of a portion of body 16 that forms the cantilevered first arm 72. As further shown in FIGS. 4A and 4B, the electrode receiving space 71 is opened up more widely in the flexed position for receiving the post 61 of electrode 60 as shown in FIG. 4C. Thus, the gripping force along the line of the opposing arrows 126 as shown in FIGS. 4A, 4B and 4C will spread the ends 73, 83 of the arms in a direct line to allow engagement with post 61 of the electrode 60. The greater the gripping or squeezing force, the greater the movement of arm 72 in the flexed position and the wider the distance between ends of the arms. The connector structure 12 may then be moved down vertically onto the electrode post as shown by arrow 140 in FIG. 4C. The opened space 71 allows the connector to receive the post head portion 62.

FIGS. 5A-5C show the connector structure 12 engaged with post 61 of electrode 60. As shown in FIGS. 5A and 5B, the gripping force has been released and the flexible cantilevered first arm 72 is free to flex back toward its rest position, thus moving arm 73 and the respective teeth 101 back in the opposite direction of arrow 130 toward end 83 and the respective contact 20. As such, teeth 101 on the cantilevered first arm 72, and particularly the arm end 73, will force the respective contact against the waist portion 64 of the electrode post 61 to provide electrical contact. The space 70 and the arms of the connector are configured to be smaller than the diameter of the electrical post. In that way, the flexed arm 72 does not return completely to its rest position. Rather, it provides spring action gripping force on the post. Specifically, referring to FIG. 5C, the electrode post 61, and particularly the waist portion 64 of that post will be gripped and held between contact and teeth 101. When the connector structure is gripped and squeezed as shown in FIG. 4B, the separated ends 73, 83 may slide over the larger head portion 62 of the post and down to the smaller diameter waist portion 64. Then when the connector structure 12 is released to return toward its rest position, the ends grab and grip the waist portion 64 to provide a good and robust electrical contact. As noted herein, the connector structure may be configured to have a thickness that is greater than the height "H" of the post 61 as shown in FIG. 3C. In that way, the complete electrode post 61 is captured inside of connector structure 12 as shown in FIG. 5C.

In accordance with another aspect the invention, the smaller diameter waist portion 64 resting beneath the larger diameter head portion 62 prevents the connector structure 12 from sliding off the electrode 60. That is, the gripping force provided by the cantilevered first arm and the second arm grip the smaller diameter waist portion 64 and thus will not pass over the larger diameter head portion, until the connector structure is again gripped and squeezed as shown in FIGS. 4A-4C. Thus, the connector structure of the invention is securely held onto the electrode 60 to provide the capture of desirable electrical signals until it is specifically removed.

While the disclosed embodiment illustrates an electrode post 61 that is shorter than the overall thickness of the connector, an alternative embodiment of the invention might incorporate a lower post, such as a second head portion and waist portion in a longer post, so that both of the contacts 20a, 20b will contact the post 61 for the electrical connection. Accordingly, the electrical connector 10 of the invention is not limited in its dimensions to only the electrode and post as illustrated, but may be used on other electrode posts having a different configuration, such as a longer post or multiple waist portions 64. Furthermore, the electrical connector 10 can be configured for a variety of different electrode dimensions such that the size of the electrode receiving space 71 may be varied to robustly grip an electrode post as the arm 72 flexes back toward its rest position.

Generally, the body 16 will be formed with arms 72, 78 so that the distance "D" between the opposing first and second arms 72, 78 in the rest position is smaller than the outer diameter of the waist portion 64 of post 61. In that way, when the connector structure 12 is released and the arm 72 returns toward the rest position, the connector structure 12 grips post 61 as shown in FIGS. 5A-5C, and a suitable gripping force is applied against the waist portion 64 of the electrode posts 61 for a good electrical connection. In one embodiment of the invention, the squeeze force required to move arm 72 and open the connector structure 12 to receive the electrode post may be in the range of 15-45 Newtons (N). The force at 90 degrees to then remove or peel off the connector structure would be in the range of 1-6 Newtons. The grip force provided on the electrode post may then be in the range of 0.1-2 Newtons.

Various embodiments as illustrated in FIGS. 1-5C are directed to a connector structure 12 that may terminate a cable 14. In one particular use of the invention, a plurality of connector structures 12 are incorporated into an assembly to interface with a plurality of electrodes positioned at different locations on a body. To that end, various connector structures may be incorporated into different connector assemblies with cables that terminate in a single connector, such as for plugging into a piece of medical equipment, such as an EKG monitor. FIGS. 7A and 7B illustrate assemblies 160 and 170 that incorporated a plurality of connector structures that terminate in a single plug.

Referring to FIG. 7A, a plurality of connector structures 12 as illustrated in FIG. 1 and other figures are coupled together, through respective cables 14, to a plug structure 162 for plugging into a piece of equipment. Each of the cables 14 incorporates one or more wires or conductors 110 that are coupled to the electrical contact assembly 20 of the connector structures 12. Each of the connector structures terminates a cable 14 and may then be placed on an appropriate electrode to capture electrical signals which are then directed through the cables 14 to the plug 162 and then to an attached piece of equipment (not shown) which interfaces with the plug 162. The plug 162 may take any appropriate form for directing the signals from the various electrical connector structures 12 for further processing. FIG. 7A illustrates five individual terminal connector structures in the assembly 160. However, a greater or lesser number of connector structures may be utilized depending upon the application of the assembly 160. As noted, each of the connector structures 12 shown in the assembly 160 will terminate the respective cable 110 and may take the form of the connector structures in FIGS. 1-5C.

Figure 6A:
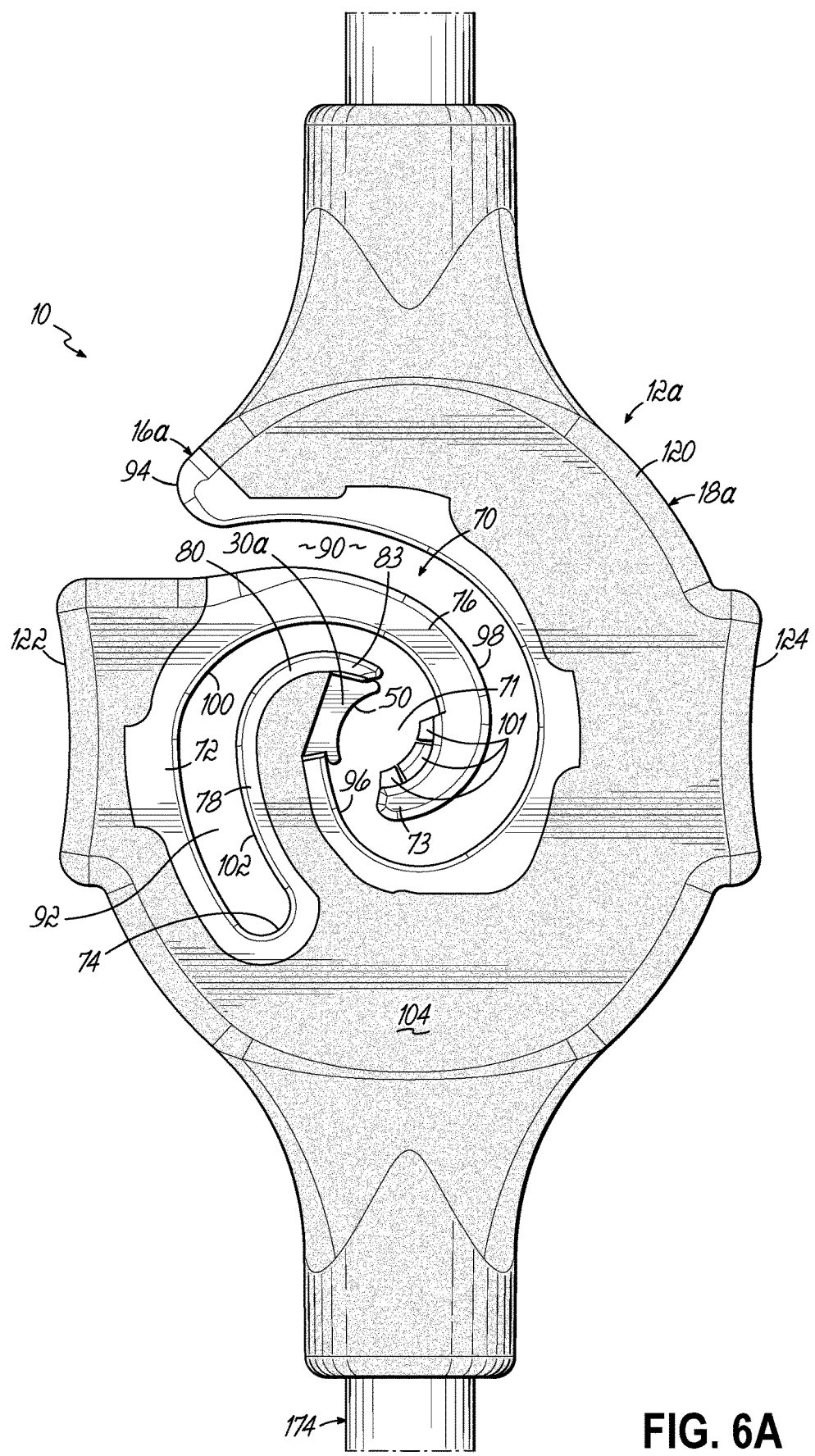
FIG. 6A is a plan view of a connector structure in accordance with another embodiment of the invention for use in a cable pass-through construction.
Figure 6B:
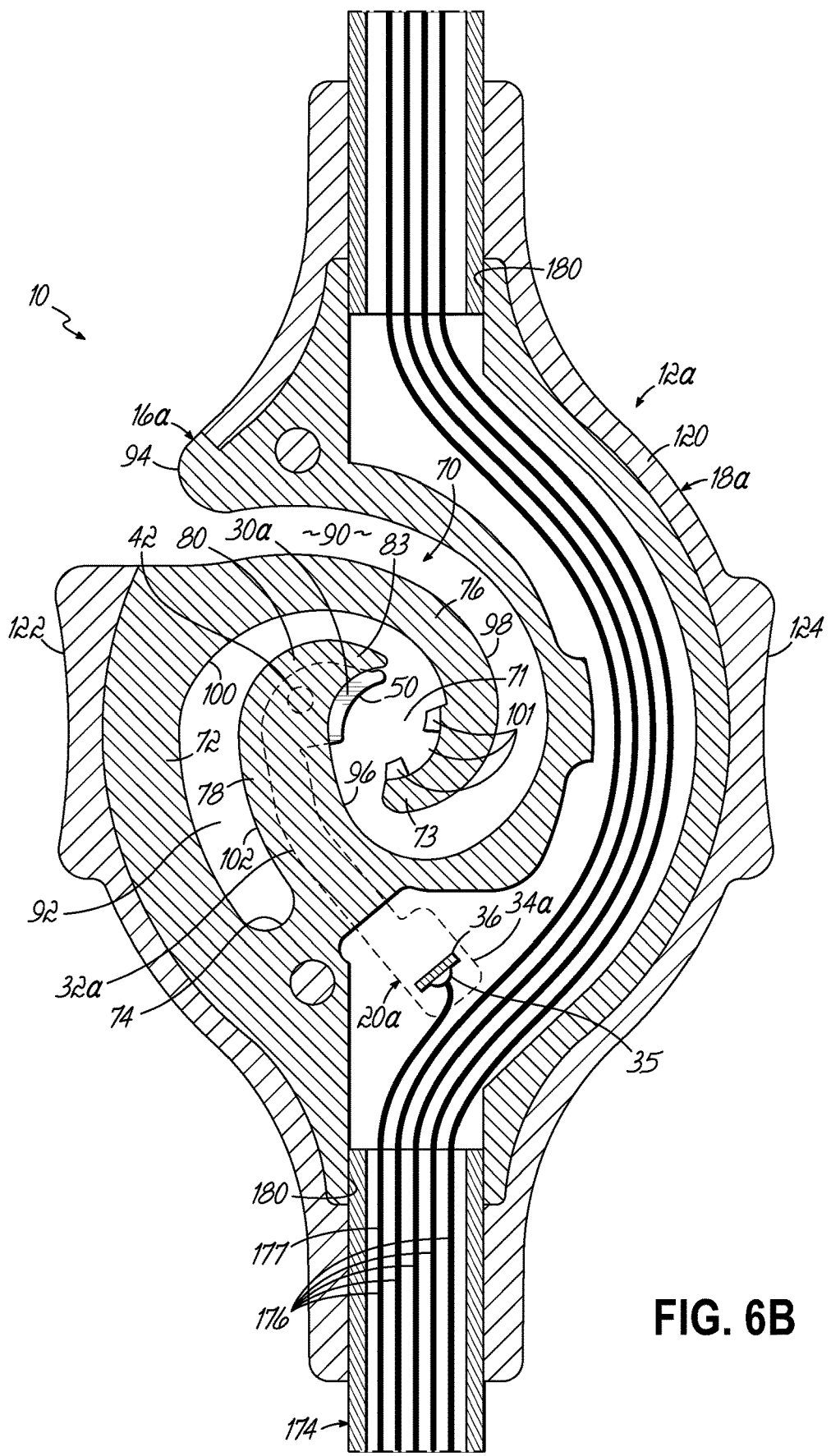
FIG. 6B is a plan view, in partial cross-section, of the connector structure of FIG. 6A.

In an alternative embodiment of the invention, each of the connector structures may be incorporated in a sequential pattern along the length of a single cable wherein a plurality of wires progress through the cable and couple sequentially with individual connector structures. Referring to FIG. 7B, assembly 170 incorporates a plug 172 which receives a cable 174 having a plurality of individual wires or conductors 176. Individual connector structures 12a are coupled along cable 174 in a sequential fashion as illustrated in FIG. 7B. Each of the connector structures 12a includes similarly functioning opposing arms and electrical contacts, but the form factor of the body 16 and the outer housing 18 that is formed over a body 16 is varied to provide the pass-through of each of the cable sections of cable 176 between the various connector structures 12a. The body 16 has a slightly different form to allow for the pass-through of cable 174. FIGS. 6A and 6B illustrate one suitable connector structure 12a.

As illustrated in FIG. 7B, a plurality of individual wires pass through cable 174 and one wire will be separated off and coupled with the particular contact 20 of a connector structure 12a. The additional wires 176 will then pass through the connector structure 12a and along the next cable section, shown sequentially as sections 174a, 174b, 174c and 174d and the wires will then couple with each sequential connector structure 12a reducing the number of individual wires 176 in each cable section until the cable terminates into a terminal connector structure 12 as illustrated in FIG. 7B. The present invention is not limited to a number of individual wires 176 progressing in cable 174, but for illustrative purposes, FIG. 7B is shown with a sufficient number of wires 176 for electrically coupling with each of the individual connector structures 12a, 12 through the length of cable 174.

Turning now to FIGS. 6A and 6B, a pass through connector structure 12a is shown in accordance with one embodiment of the invention. As noted, the functional features including the cantilevered first arm 72 as well as the stationary second arm 78 are generally similarly formed in the pre-formed body 16a and operate similarly as described with respect to FIGS. 1-5C. However, the connector structure 12a, and particularly the body 16a incorporates an input port 180 and an output port 182 for interfacing with sections of cable 174 to provide a sequential arrangement of the electrodes and essentially the pass-through of the cable 174 and the individual wires or conductors 176 therein to each of the sequential connector structures 12a as illustrated in FIG. 7B. More particularly, a cable 174 or appropriate cable section, with individual wires 176 is directed into port 180 for a connector structure 12a. One of the wires 177 is separated and is individually electrically coupled to an electrical contact assembly 20, such as by a solder junction 35 with a contact pad 34a, 34b or the extension leg 36. The remaining wires 176 are then passed through appropriate open space 184 formed in housing 16a and passed through another portion of cable 174 to the next sequential connector structure 12a. In that way, the wires proceed until terminated, such as in a terminal conductor structure 12 as shown in FIG. 7B. The over mold housing 18a is similarly formed as described with respect to FIGS. 1-5C and has opposing portions for squeezing the connector structure and moving the cantilevered first arm 72 with respect to the stationary second arm 78. In that way, the connector structures of the various assemblies 160, 170 as illustrated in FIGS. 7A and 7B are used to connect with a number of electrodes 60 positioned on the body for the collection of electrical signals for further processing and analysis. The connector structures provide a direct line of travel of the cantilevered arm and stationary arm when opening and closing the connector structure on an electrode. Such a direct travel and grip connection of the electrode provides a desirable and robust electrical connection. The connector structures stay firmly attached to the electrode and can be removed only by again squeezing the connector structure to move the cantilevered arm away from the stationary arm in order to provide suitable clearance for pulling the connector structure from an electrode.

While the present invention has been illustrated by a description of various embodiments and while these embodiments have been described in some detail, it is not the intention of the inventors to restrict or in any way limit the scope of the appended claims to such detail. Thus, additional advantages and modifications will readily appear to those of ordinary skill in the art. The various features of the invention may be used alone or in any combination depending on the needs and preferences of the user.

What is claimed is:

1. A connector for coupling with an electrode, the connector comprising:

a body, the body configured for forming an internal space;

a cantilevered arm having a hinge point and an end, the cantilevered arm extending from the hinge point toward the internal space, the cantilevered arm having a rest position and a flexed position;

a stationary arm having a base on the body proximate to the hinge point of the cantilevered arm and an end, the stationary arm extending from the base into the internal space;

the cantilevered arm extending in the internal space around a portion of the stationary arm and positioning the end of the cantilevered arm proximate the end of the stationary arm;

in the rest position, the end of the cantilevered arm positioned from the end of the stationary arm a first distance in the internal space;

in the flexed position, the cantilevered arm flexing at the hinge point and moving the end thereof away from the end of the stationary arm to separate the ends to a second distance for receiving an electrode in the internal space;

the cantilevered arm configured for flexing at the hinge point back toward the rest position to grip the electrode.

2. The connector of claim 1 wherein the cantilevered arm and stationary arm are configured for positioning the respective arm end of the cantilevered arm to move to separate the ends to the second distance.

3. The connector of claim 1 wherein at least one of the ends of the cantilevered arm and stationary arm includes an electrical contact, the electrical contact gripping the electrode when the cantilevered arm flexes back toward the rest position.

4. The connector of claim 3 wherein at least another one of the ends of the cantilevered arm and stationary arm includes teeth, the teeth gripping the electrode against the electrical contact when the cantilevered arm moves flexes back toward the rest position.

5. The connector of claim 3 wherein the stationary arm includes the electrical contact.

6. The connector of claim 1 wherein the cantilevered arm is configured to extend in a spiral path around the portion of the stationary arm for positioning the end of the cantilevered arm opposite the end of the stationary arm in the internal space.

7. The connector of claim 1, the connector further comprising gripping portions positioned proximate opposing sides of the body, at least one of the gripping portions positioned proximate the cantilevered arm so that a gripping force applied to the gripping portions hinges the cantilevered arm at the hinge point from the rest position to the flexed position.

8. The connector of claim 1 wherein the cantilevered arm and stationary arm are integrally formed with the body.

9. The connector of claim 7 further comprising an overmold structure molded over the body, the gripping portions formed by the overmold structure.

10. A connector assembly for coupling with at least one electrode, the connector assembly comprising:
at least one cable having at least one wire;
a plug electrically coupled with an end of the at least one cable;
at least one connector structure electrically coupled with the at least one cable, the connector structure comprising:
a body, the body configured for forming an internal space;
a cantilevered arm having a hinge point and an end, the cantilevered arm extending from the hinge point toward the internal space, the cantilevered arm having a rest position and a flexed position;
a stationary arm having a base on the body proximate to the hinge point of the cantilevered arm and an end, the stationary arm extending from the base into the internal space;
the cantilevered arm extending in the internal space around a portion of the stationary arm and positioning the end of the cantilevered arm proximate the end of the stationary arm;
at least one of the ends of the cantilevered first arm and stationary second arm including an electrical contact coupled to a wire of the cable;
in the rest position, the end of the cantilevered arm positioned from the end of the stationary arm a first distance in the internal space;
in the flexed position, the cantilevered arm flexing at the hinge point and moving the end thereof away from the end of the stationary arm to separate the ends to a second distance for receiving an electrode in the internal space;
the cantilevered arm configured for flexing at the hinge point back toward the rest position to grip the electrode against the electrical contact.

11. The connector assembly of claim 10 wherein the cantilevered arm and stationary arm are configured for positioning the respective arm end of the cantilevered arm to move to separate the ends to the second distance.

12. The connector assembly of claim 10 wherein at least another one of the ends of the cantilevered arm and stationary arm includes teeth, the teeth gripping the electrode against the electrical contact when the cantilevered arm flexes back toward the rest position.

13. The connector assembly of claim 10 wherein the stationary arm includes the electrical contact.

14. The connector assembly of claim 10 wherein the cantilevered arm is configured to extend in a spiral path around the portion of the stationary arm for positioning the end of the cantilevered arm opposite the end of the stationary arm in the internal space.

15. The connector assembly of claim 10 further comprising a plurality of cables, the plug electrically coupled with an end of each of the plurality of cables, a connector structure terminating each of the plurality of cables and coupled with a wire of a respective terminated cable.

16. The connector assembly of claim 10 further comprising a cable having a plurality of wires, the plug electrically coupled with an end of the cable, a plurality of connector structures positioned successively along the length of the cable, a wire of the cable coupled with a first respective connector structure along the length of the cable and additional wires of the cable passing through the first respective connector structure to couple with other respective connector structures positioned successively further along the cable.

17. The connector assembly of claim 10, the connector further comprising gripping portions positioned proximate opposing sides of the body, at least one of the gripping portions positioned proximate the cantilevered arm so that a gripping force applied to the gripping portions hinges the cantilevered arm at the hinge point from the rest position to the flexed position.

18. The connector assembly of claim 10 wherein the cantilevered arm and stationary arm of the connector structure are integrally formed with the body.

19. The connector assembly of claim 17 wherein the connector structure further comprises an overmold structure molded over the body, the gripping portions formed by the overmold structure.

20. A connector assembly for coupling with at least one electrode, the connector assembly comprising:
a plurality of cables, each having at least one wire;
a plug electrically coupled with respective ends of the plurality of cables;
a connector structure electrically coupled with and terminating a respective one of the plurality of cables, the connector structure coupled with a wire of a respective terminated cable, at least one of the connector structures comprising:
a body, the body configured for forming an internal space;
a cantilevered arm having a hinge point and an end, the cantilevered arm extending form the hinge point toward the internal space, the cantilevered arm having a rest position and a flexed position;
a stationary arm having a base on the body proximate to the hinge point of the cantilevered arm and an end, the stationary arm extending from the base into the internal space;

the cantilevered arm extending in the internal space around a portion of the stationary arm and positioning the end of the cantilevered arm proximate the end of the stationary arm;

at least one of the ends of the cantilevered first arm and stationary second arm including an electrical contact coupled to a wire of the cable;

in the rest position, the end of the cantilevered arm positioned from the end of the stationary arm a first distance in the internal space;

in the flexed position, the cantilevered arm flexing at the hinge point and moving the end thereof away from the end of the stationary arm to separate the ends to a second distance for receiving an electrode in the internal space;

the cantilevered arm configured for flexing at the hinge point back toward the rest position to grip the electrode against the electrical contact.

\* \* \* \* \*